(12) United States Patent
Rosenblatt et al.

(10) Patent No.: US 11,446,408 B2
(45) Date of Patent: Sep. 20, 2022

(54) COMPOSITION AND METHODS FOR ANTIMICROBIAL ARTICLES

(71) Applicant: SOLOMON ROSENBLATT, Key West, FL (US)

(72) Inventors: Solomon Rosenblatt, Key West, FL (US); John P. Kennedy, Pooler, GA (US); Curtis E. Jones, Savannah, GA (US)

(*) Notice: Subject to any disclaimer, the term of this patent is extended or adjusted under 35 U.S.C. 154(b) by 0 days.

(21) Appl. No.: 14/923,430

(22) Filed: Oct. 27, 2015

(65) Prior Publication Data

US 2016/0045637 A1 Feb. 18, 2016

Related U.S. Application Data

(62) Division of application No. 13/713,908, filed on Dec. 13, 2012, now abandoned.

(60) Provisional application No. 61/630,596, filed on Dec. 16, 2011.

(51) Int. Cl.
| | |
|---|---|
| *A61L 24/00* | (2006.01) |
| *A01N 31/02* | (2006.01) |
| *C08L 29/04* | (2006.01) |
| *A01N 59/12* | (2006.01) |
| *C08J 9/26* | (2006.01) |
| *A61L 24/02* | (2006.01) |
| *A61L 24/04* | (2006.01) |
| *A61M 1/00* | (2006.01) |

(52) U.S. Cl.
CPC .......... *A61L 24/0036* (2013.01); *A01N 31/02* (2013.01); *A01N 59/12* (2013.01); *A61L 24/0015* (2013.01); *A61L 24/02* (2013.01); *A61L 24/043* (2013.01); *A61M 1/0023* (2013.01); *C08J 9/26* (2013.01); *C08L 29/04* (2013.01); *A61L 2300/106* (2013.01); *A61L 2300/404* (2013.01); *C08J 2201/026* (2013.01); *C08J 2329/04* (2013.01)

(58) Field of Classification Search
None
See application file for complete search history.

(56) References Cited

U.S. PATENT DOCUMENTS

| | | | |
|---|---|---|---|
| 1,867,222 A | 7/1932 | Karns | |
| 2,381,621 A | 8/1945 | Schmelkes et al. | |
| 3,328,259 A | 6/1967 | Anderson | |
| 3,817,860 A | 6/1974 | Lambert et al. | |
| 3,923,665 A | 12/1975 | Lambert et al. | |
| 4,031,209 A | 6/1977 | Krezanoski | |
| 4,098,728 A | 7/1978 | Rosenblatt | |
| 4,128,633 A | 12/1978 | Lorenz et al. | |
| 4,178,361 A | 12/1979 | Cohen et al. | |
| 4,255,415 A | 3/1981 | Chrai et al. | |
| 4,323,557 A | 4/1982 | Rosso et al. | |
| 4,340,043 A | 6/1982 | Seymour | |
| 4,396,642 A | 8/1983 | Bolt et al. | |
| 4,552,138 A | 11/1985 | Hofeditz et al. | |
| 4,675,009 A | 6/1987 | Hymes et al. | |
| 4,863,972 A | 9/1989 | Itagaki et al. | |
| 5,071,648 A | 12/1991 | Rosenblatt | |
| 5,085,781 A | 2/1992 | Tsuru et al. | |
| 5,170,580 A | 12/1992 | Rosenblatt | |
| 5,276,993 A | 1/1994 | Rosenblatt | |
| 5,370,656 A | 12/1994 | Shevel | |
| 5,447,505 A | 9/1995 | Valentine et al. | |
| 5,466,231 A | 11/1995 | Cercone et al. | |
| 5,554,658 A | 9/1996 | Rosenblatt | |
| 5,554,659 A | 9/1996 | Rosenblatt | |
| 5,556,391 A | 9/1996 | Cercone et al. | |
| 5,589,072 A | 12/1996 | Shanbrom | |
| 5,679,371 A | 10/1997 | Tanihara et al. | |
| 5,744,150 A | 4/1998 | Cercone | |
| 5,811,471 A | 9/1998 | Shanbrom | |
| 5,843,060 A | 12/1998 | Cercone | |
| 5,928,665 A | 7/1999 | Cercone | |
| 6,027,573 A | 2/2000 | Cercone et al. | |
| 6,080,092 A | 6/2000 | Cercone et al. | |
| 6,099,952 A | 8/2000 | Cercone | |
| 6,103,018 A | 8/2000 | Cercone et al. | |
| 6,169,123 B1 | 1/2001 | Cercone | |
| 6,214,895 B1 | 4/2001 | Cercone | |
| 6,235,125 B1 | 5/2001 | Cercone et al. | |
| 6,264,972 B1 | 7/2001 | Drury | |
| 6,329,438 B1 | 12/2001 | Cercone et al. | |
| 6,365,169 B1 | 4/2002 | Rosenblatt | |
| 6,793,612 B1 | 9/2004 | Cercone et al. | |
| 6,875,163 B2 | 4/2005 | Cercone et al. | |
| 8,298,582 B2 | 10/2012 | Gastonguay et al. | |
| 2006/0276108 A1* | 12/2006 | Benson | A46B 13/008 451/41 |

(Continued)

OTHER PUBLICATIONS

Wound (https://en.wikipedia.org/wiki/Wound (downloaded on Dec. 9, 2016)).*
Otitis (https://en.wikipedia.org/wiki/Otitis (downloaded Dec. 9, 2016)).*
Merocel (http://www.merocel.com/products/index.htm (downloaded on Dec. 9, 2016).*
Negative Pressure Wound Therapy (2007).*
Merocel (http://www.merocel.com/products/index.htm (downloaded Dec. 9, 2016).*

*Primary Examiner* — Jake M Vu

(74) *Attorney, Agent, or Firm* — Nixon & Vanderhye P.C.

(57) ABSTRACT

A biocompatible controlled release form of complexed iodine is achieved by a complexation of polyvinyl alcohol based foam and characterized by a residual starch component to optimize iodine release profiles. The resulting iodine complexed polyvinyl alcohol foam may be utilized locally as an antimicrobial agent that releases controlled amounts of iodine sufficient to kill microbes for extended durations without excessive bulk and rigidity.

28 Claims, 1 Drawing Sheet

(56) References Cited

U.S. PATENT DOCUMENTS

2008/0248135 A1* 10/2008 Hirsh .................. A61K 9/0046
424/667
2009/0131537 A1* 5/2009 Wille, Jr. ............... A61K 31/07
514/725
2010/0298791 A1* 11/2010 Jones ................ A61F 13/00012
604/319

* cited by examiner

COMPOSITION AND METHODS FOR ANTIMICROBIAL ARTICLES

RELATED APPLICATIONS

This application is a divisional of application Ser. No. 13/713,908, filed Dec. 13, 2012, pending; which claims priority benefit of Application No. 61/630,596, filed Dec. 16, 2011; the entire contents of each of which are herein incorporated by reference.

BACKGROUND OF THE INVENTION

Field of the Invention

This invention relates to polymeric foams, sponges and gels produced with carbohydrate pore formers to produce unique foam densities, and more particularly, complexes of specific density PVA foams with iodine that exhibit specific release profiles and durations of release to impart antimicrobial activity in a controlled and specific manner.

Background of the Invention

Iodine is an outstanding microbiocide, with an extraordinary range of action. Part of its mode of action is that it is able to penetrate the cell walls of microorganisms rapidly, and block certain essential hydrogen-bonding in amino acids. Also, it has a powerful, oxidizing effect on S—H, —S—S— groups, which are essential factors in protein production. It is effective against a wide range of microorganisms, including bacteria, tubercle bacilli (Mycobacteria), fungi, protozoa, lipid and medium viruses, as well as non-lipid and small viruses. Iodine is designated as an intermediate germicide only because spores are not readily killed with weak concentrations. However, iodine has the greatest microbial efficiency compared to the other halogens, chlorine and bromine, since it is deactivated by proteins at least three times slower than chlorine and four times slower than bromine. Therefore, under normal conditions of use where there is the presence of large amounts of dissolved proteins as in blood, serum, or sputum, iodine would not be rendered ineffective. Iodine has the additional advantage that its disinfecting properties are independent of the pH value of its environment. Therefore, unlike chlorine, for example, iodine would not be rendered ineffective in an acid pH. It would likewise not be deactivated quickly in an alkaline pH.

Low concentrations of iodine react relatively slowly as compared with proteins in general and therefore it remains available to react with bacteria to which it generally has a greater affinity. In this manner iodine can exhibit its unique advantageous selectivity towards microorganisms while maintaining a very low level of cytotoxicity to the host cells. However, because of iodine's physical and inherent chemical properties, its use as an antiseptic, broad-spectrum antimicrobial has been limited because state of the art delivery methods allows for the liberation of too much free iodine which can be toxic to living cells.

Elemental iodine, in the form of Tincture of Iodine (alcoholic solution), is highly toxic if brought into contact with the body cavity. It causes swelling and bleeding of the mucous membranes. Iodine is therefore generally not impregnated into bandages because of the potential for this corrosive destruction of the skin. A 1% Tincture of Iodine solution can release in excess of 10,000 PPM of iodine into the surrounding tissue environment all at once, when only 0.2 PPM of iodine may be required to be antimicrobially effective. Consumption by an adult of 30 grams of Tincture of Iodine can be fatal. Also, elemental iodine is volatile having a high, intrinsic vapor pressure that causes, over time, a loss in microbial cidal potency. This occurs when the iodine content volatizes from coated surfaces or from antiseptic preparations, especially when exposed to the environment at elevated temperatures.

One example of an attempt to preserve or tame the outstanding antimicrobial activity of iodine, while simultaneously reducing its corrosive toxic and vapor pressure properties, is a two-part dressing, using an iodide salt in one component and an oxidizer in the other, which react on moisture contact, liberating iodine, as in U.S. Pat. No. 1,867,222. Another example is the use of water-soluble complexes of polyvinyl pyrrolidone iodine complex (PVP/I) as disclosed in U.S. Pat. No. 4,128,633. The latter is illustrative of a complex of iodine and an organic carrier commonly known as an iodophor. This complexing of iodine "harnesses" the iodine, thereby controlling its rate of release. The former describes a delayed release mechanism for free iodine. However, both these aqueous solution complexes still have limited application in spite of their slower release properties, as their water miscibility with body fluids still causes excess delivery and quick dissipation of the released iodine, resulting in possible cytotoxicity and loss of long time effectiveness.

Iodophors are loose complexes of elemental iodine or triodide, solubilizers, and a polymeric carrier that serves, not only to increase the solubility of the iodine, but also to tame the iodine to provide a sustained release reservoir for the iodine. The carriers, heretofore, have been neutral, water-soluble polymers, with mainly polyvinyl pyrrolidones as the principal commercialized polymer. Polyether glycols, polyacrylic acids, polyamides, polyoxyalkylenes, starches and polyvinyl alcohol also form iodophors. Carriers may also exhibit varying degrees of surface-active properties that improve the penetration or wetting characteristics of the solution in use. Upon dilution, these iodophor complexes form micellar aggregates, which are dispersed, upon dilution, with water or bodily fluids, and the iodine linkage to the polymer is progressively weakened until the iodine can be regarded as free to generate antimicrobial concentrations. These iodine complexes in aqueous solution have the advantage over pure, elemental iodine solutions, in that because they are present in far less concentration they greatly reduce irritation to tissue, unpleasant odor, staining of tissue and corrosion of metal surfaces such as surgical instruments, but dissipate relatively quickly because of their miscibility and reaction with body fluids.

Generally, when such a complex is in equilibrium with the aqueous phase, and then diluted, the solution will have increased availability of free iodine within a given fixed volume. These iodophors, because of their water solubility, therefore tend to dissipate their antimicrobial action quickly, because as a solution, they are water miscible with fluids throughout the wound site, and react relatively quickly with serous fluids while reacting with the bacteria. The concentrations of iodine in water-based systems can be much higher than what is required for its antimicrobial intent, and iodine is dissipated by side reactions with body fluids, resulting in the iodine reservoir being prematurely used up and thus allowing recolonization of the wound site.

Compared to Tincture of Iodine, the improved release properties of PVP/I iodophors have resulted in the greater use of iodine in preoperative skin preps, surgical scrubs, washes, douches, lotions and ointments. However, their limited iodine reserves and dilution factors have meant that such iodophors are effective for a given disinfecting purpose for a limited time only. Microorganisms that have survived the initial application, because of limited longevity of the antimicrobial agent, may act as a seed to cause the pathogen population to rise again to its initial level.

Most water miscible broad-spectrum antimicrobials exhibit this deficiency. Continuous application of the antimicrobial agent to the site is therefore required, to inhibit the increase in population. For example, sustained release can be provided, with prolonged antibacterial activity under a plastic, self-adhering surgical drape film. U.S. Pat. No. 4,323,557 describes a process for incorporating N-Vinyl-Pyrrolidone (NVP) in the polymeric backbone of a pressure-sensitive adhesive of which the pyrrolidone component serves to complex and slowly release the iodine. The iodophor-based adhesive film provides a sterile operative surface, and acts as a barrier to isolate the incision from contaminating skin flora. This product is for use as an incisible self-adhering drape and is not intended for wound healing dressings or wound packings.

A major disadvantage of PVP/I complexes is that their safe and efficacious antimicrobial action is limited by recommendation to use on skin alone. This is primarily due to their water solubility, as mentioned above, resulting in excess releases of free iodine when introduced to vital tissues (i.e. broken skin). Considering that as little as 0.2 PPM of iodine is sufficient to kill enteric bacteria (10 minutes at 25 degrees Celsius), and under the same conditions, 3.5 PPM and 14.6 PPM of iodine, respectively, are sufficient to kill amoebic cysts and enteric viruses, PVP/I complex solutions can instantaneously introduce thousands of excess parts of available iodine in one bolus (i.e., an uncontrolled burst of solution), dependent upon the site. Large concentrations of free iodine, as with borates, are cytotoxic and cytopathic to healthy tissue, and can have an adverse affect of reducing the body's natural defense mechanism against infection.

PVP/I solutions are administered to open wound sites, as in burns, even though they are toxic, when stopping infection takes precedence over proper wound healing. Typical commercial antibacterials such as soap, Hexachlorophene, Hibiscrub, alcohol, and Chlorhexidine are all water-soluble and water miscible preparations, which exhibit various efficacious antimicrobial properties on the skin, but all, are relatively toxic upon contact with living cells and known to produce resistant strains of bacteria.

Iodine complexes with an alternative to PVP are known in the art. U.S. Pat. No. 5,071,648 describes a process for complexing air foamed PVA foam with iodine to overcome the deficiencies of the foregoing antimicrobial solutions. However, the resulting complexed foams from the method of U.S. Pat. No. 5,071,648 result in a relatively low-density final product. These low densities fail to provide the lateral pressure to prevent the dislodgment of articles placed in the auditory canal. Later designs that included a hollow opening to prevent hearing loss during treatment further weakened the lateral expansion forces and exacerbated dislodgment of the implanted devices (falling out of ear during normal activity). The low-density contribution to unacceptable lateral strength to prevent unintended dislodgment alone, made these devices fail commercially in pilot testing. Further, such relatively low densities require high bulk and weight dressings for wound treatment, which reduce the flexibility and comfort of these dressings when applied in practice. These relatively low density foams also limit absolute iodine dosing and more importantly the duration of iodine release which mandates the wound dressing or implant be changed more frequently. The more rapid release of iodine from this process not only decreases the duration of release, but also pushes iodine toxicity to undesirable levels. Patient pain is also significant for these devices due to the limited flexibility. Ultimately such limitations have prevented the commercialization of U.S. Pat. No. 5,071,648.

Iodine complexes PVA are also described in U.S. Pat. No. 6,365,169. This prior art is limited to and describes a process for complexing air foamed PVA foam with iodine to provide a method for preparing a PVA coating for depositing upon, and interstitially onto, a variety of readily available, inexpensive devices. The PVA, once coated onto a suitable substrate is subsequently complexed with iodine to produce controlled iodine release coated materials. U.S. Pat. No. 6,365,169 further combined PVA with other iodine complexation substrates including starches, to produce PVA foams with these iodine complexing substrates as a permanent integral component of the resulting polymerized foam. However, as U.S. Pat. No. 6,365,169 still relied upon the air foaming process, the resulting complexed foams from the method of U.S. Pat. No. 6,365,169 results in a relatively low density final product as before with all the limitations previously described including higher bulk, lower dose per size, lower flexibility per dose, shorter durations of iodine release, and higher toxicity. Ultimately such limitations have prevented the commercialization of U.S. Pat. No. 5,071,648 to date.

RELATED ART

A search of the prior art did not disclose any patents that read directly on the claims of the instant invention; however, the following references were considered related.

| Number | File Date | Inventor(s) |
|---|---|---|
| 5,071,648 | March 1990 | Solomon Rosenblatt |
| 6,365,169 | September 1999 | Solomon Rosenblatt |
| 4,675,009 | June 1987 | Hymes et al. |
| 4,552,138 | November 1985 | Hofeditz et al. |
| 4,396,642 | August 1983 | Bolt et al. |
| 4,340,043 | July 1982 | Seymour |
| 4,323,557 | April 1982 | Rosso et al. |
| 4,255,415 | March 1981 | Chrai et al. |
| 4,128,633 | December 1978 | Lorenz |
| 4,031,209 | June 1977 | Krezanoski |
| 3,328,259 | June 1967 | Anderson |
| 2,381,621 | August 1942 | Schmelkes et al. |
| 1,867,222 | July 1932 | Karns |

SUMMARY OF THE INVENTION

It is the central object of this invention to overcome the deficiencies of the foregoing complexed PVA foams, by increasing the density of the PVA foam through an improved process including complexation. The prior art air foaming process utilized for U.S. Pat. Nos. 5,071,648 and 6,365,169 produces relatively lower density foams with coarser textures.

It is a further object of this invention to overcome the deficiencies of the foregoing complexed PVA foams, by reducing the bulk size by thickness and volume to provide smaller devices for tight anatomical spaces and to provide for thinner, more flexible, and smoother, less painful surface textures and thicknesses.

It is a further object of this invention to overcome the deficiencies of the foregoing complexed PVA foams, by reducing the toxicity related to the iodine release profiles (concentration at 3, 6, and 12 hours) exhibited by U.S. Pat. Nos. 5,071,648 and 6,365,169 specimens.

It is a further object of this invention to overcome the deficiencies of the foregoing complexed PVA foams, by reducing the toxicity related to the iodine release profiles by extending the durations exhibited by U.S. Pat. Nos. 5,071,648 and 6,365,169 specimens.

It is a further object of this invention to overcome the deficiencies of the foregoing complexed PVA foams, by reducing the toxicity related to the excess iodine potential exhibited by U.S. Pat. Nos. 5,071,648 and 6,365,169 processing techniques.

It is a further object of this invention to overcome the deficiencies of the foregoing complexed PVA foams, by reducing the potential for unnecessary patient pain by the addition of lipid based semi-solids that still provide excellent release profiles.

DESCRIPTION OF SPECIFIC EMBODIMENTS OF THE INVENTION

Definitions

Figure 1:
FIG. 1 shows an electron micrograph of the lower density PVA foam of the prior art produced by the entrapped air foaming process.
Figure 2:
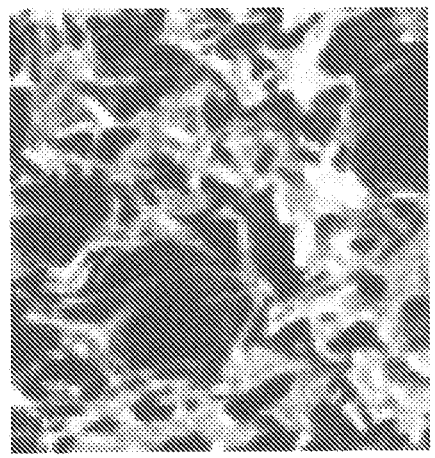
FIG. 2 shows an electron micrograph of the high density PVA foam of the claimed invention produced by the pore former foaming process.

As used in this description and the accompanying claims, the following terms shall have the meanings indicated, unless the context otherwise requires:

"Entrapped Air Foaming Process" as broadly defined and used herein, means any process for producing PVA foam that utilizes the intentional entrapment of air bubbles, ultimately ruptured during or after polymerization, to produce an insoluble PVA porous foam and specific density.

"Pore Former Foaming Process" as broadly defined and used herein, means any process for producing PVA foam that utilizes a pore forming particle, at least partially removed subsequent to polymerization, to produce an insoluble PVA porous foam and specific density. The microstructure and density of PVA foam produced by this process is distinctive from the air entrapped air foaming process as shown in the figures and described herein.

"Shaker Bath Release Testing Method" as broadly defined and used herein, is paraphrased from the United States Pharmacopeia (USP Apparatus 2), modified to accommodate wound dressings via controlled temperature shaker baths. The apparatus as modified consists of the following: covered vessel(s) made of glass or other inert, transparent material, optionally held within a rack; the vessel(s) or rack of vessels positioned upon a lateral shaker tray to provide agitation of the media and samples within each vessel; a motor; a motor drive shaft; and a rocker arm. Each vessel is partially immersed in a suitable water bath of any convenient size that accommodates the lateral agitation. The water bath includes a lid over the bath and permits holding the temperature inside the vessel at 37±2° during release testing and keeping the bath fluid in constant, smooth motion. No part of the assembly, including the environment in which the assembly is placed, contributes significant motion, agitation, or vibration beyond that due to the gently rocking tray intended for controlled agitation. The sample vessels are cylindrical, with a flat bottom and with the following dimensions and capacities: for a nominal capacity of 18 ml, the height is 160 mm to 210 mm and its inside diameter is 98 mm to 106 mm. A fitted cover (cap) composed of inert material may be used to retard evaporation. The rocker arm is mounted by any number of means to a motor drive shaft, so as to produce a full lateral tray shift (shake) of 0.5 inch±10%. The rocker and shaft union produces a smooth lateral shift of the tray without significant vibration or wobble. A speed-regulating device is used that allows the shaft rotation speed to be selected and maintained at the rate specified by the method within ±10%, which accordingly determines the lateral shifts per minute. Unless otherwise specified, specimens are placed into dry vessels and adapted to cover the bottom of the vessel before dissolution media is charged on top of specimen within the vessel, the specimen/vessel is placed upon the tray and the testing begins. Specimens that tend to float may be covered with 10 mesh stainless screen if necessary and recorded.

Exemplary shaker baths are Release Shaker Bath with Microprocessor (Julabo SW23). The specifications of the method as utilized for release profile testing herein:

a) Insert=Lateral Shift Tray (shaker tray),
b) Vessel Size=1 inch 20 cc vials (fisher scientific 03-340-25Q or similar),
c) Vessel Composition=glass,
d) Closure=Screw Cap,
e) Lateral Shift=0.5 inch±10% per oscillation (half revolution),
f) Water Bath Temp=37 Celsius±2,
g) Vessel Emersion Depth=60% height±10%,
h) Drive Speed=20 rpm, and
i) Media—Distilled Water, 18 cc per vessel.

I. Improved PVA Foam Density:

The prior art for producing iodine complexed PVA foam employs an "Entrapped Air Foaming Process" (see definitions). Namely, U.S. Pat. Nos. 5,071,648 and 6,365,169 utilized exclusively this air foaming process. This air foaming process results in an uncomplexed PVA foam density of 0.024 to 0.072 g/cm$^3$ (dry). Due to size limitations of auditory canal and thickness limitations to reduce the bulk of wound dressings the need for a higher density iodine complexed PVA foam was required. The need for higher surface area and greater foam lateral strength to prevent dislodgement of auditory implants also required a more dense complexed PVA foam. Finally, the corresponding dose requirements for otic and wound preparations further drove the need for higher density foam than provide for by prior art U.S. Pat. Nos. 5,071,648 and 6,365,169.

Several attempts were made to produce high density PVA foam using the process employed for U.S. Pat. Nos. 5,071,648 and 6,365,169. Ultimately, a density of 0.072 g/cm$^3$ was achieved (densities ranged from 0.024 to a maximum of 0.072 g/cm$^3$). Unfortunately, the maximum density achieved did not solve the disadvantages disclosed above. Lateral strength and bulk were improved, but still short of design specifications. Notably, the release profile and iodine load continued to fall well short of specifications (release profile disclosed below). Therefore, process development began using a new strategy defined herein as the "Pore Former Foaming Process". Only carbohydrate pore formers were successful, however, the most attractive processes from an ease of processing and economy basis were the starch based pore formers. Unfortunately, it was well known in the art that starch particles were not biocompatible and avoided due to toxicity in animate systems when used in many devices. In fact, both U.S. Pat. Nos. 5,071,648 and 6,365,169 specifically avoid the use of starch for PVA foams intended for animate tissues. Surprisingly however, PVA foams prepared by the process described herein passed all biocompatibility testing with exemplary scores (see examples). Even more surprisingly, this lower toxicity extended to the PVA foams after complexation, presumably due to some of the iodine complexing with some of the residual starch rather than purely with the PVA foam. Accordingly, processing was subsequently optimized to obtain ideal iodine release profiles using the starch first as a pore former to produce the required density, then removing a significant portion of the starch via washing steps to provide adequate porosity, but leaving a target residual of starch to subsequently complex with iodine along with the PVA to generate the targeted release profile with lower toxicity and longer duration. The range of densities resulting from various intentional manipulations of the new process ranged from 0.074 g/cm$^3$ to 0.141 g/cm$^3$, significantly greater than the prior art process. The successful densities that satisfied the disadvantages of the prior art referenced for the uncomplexed PVA foam began at about 0.078 g/cm$^3$. Densities greater than about 0.080 g/cm$^3$ are preferred and densities greater than 0.090 g/cm$^3$ are more preferred. Due to the potency of iodine, density increases of about 10% are significant; therefore tight controls are warranted during processing to prevent the loss of density. The prior art has not foreseen the advantages of this density range and residual starch content for limiting toxicity, reducing bulk including thickness, greater material flexibility, and extending iodine release duration. The unexpected positive results from the above composition, process, and density for animate tissues occurred despite the fact that good surgical practices taught away from using starch in any medical device that comes in contact with open tissues. By way of non-limiting examples, starch used on surgical gloves is known to produce granulomas, infections, and other foreign body reactions. Further, the prior art, namely U.S. Pat. Nos. 5,071,648 and 6,365,169 also discourage the use of starch in the PVA foam systems for animate tissues. The above composition surprisingly produces biocompatible PVA based sponge specifications greater than 0.090 g/cm$^3$. The following are further benefits to the combination of PVA and residual starch using this pore former foaming process: a) the smoother surface produces less tissue ingrowth during the healing process and therefore releases easier from the tissue site causing less patient pain, b) cut to thickness sheets of the new PVA foam is more flexible in the dry state because the starch derived foam produces a fibrous pore geometry while the prior art consisted of a continuous network of smoother interconnected spherical pores which is more rigid, c) the denser pore structure results in faster wicking of exudates due to improved capillarity action, d) the denser foam puts more of the complexed foam surface in contact with the wound, e) the higher density increases strength allowing thicknesses as low as 2 mm to have adequate robustness for handling while proving easier to conform to tissue anatomy and packing, and f) maintains its moisture content, allowing an improved healing environment.

In addition to the attributes of flexibility, thickness, and smooth surfaces provided for by the claimed invention, it was discovered that packaging the complexed foam with a moisture content of at least 40% decreased patient pain upon application by providing a cooling sensation to raw tissues. Further, the residual moisture content, commonly removed to reduce shipping weight and expenses, greatly improves the handling and shaping of the material by clinicians to the anatomical site. A moisture content of at least 60% is more preferred and at least 70% is most preferred for the cooling sensation.

PVA and starch both consist of carbohydrate like components, e.g. hydroxyl groups, and only carbon and hydrogen in their chains. In the pore former foaming process when heated, starch swells to a partially soluble particle compatible with the PVA that forms the pores in the resulting foam after at least partial removal. The starch selected is in part chosen based on its particle size which influences the ultimate pore size and processing characteristics with the particular PVA resin employed, though the ultimate pore size is not necessarily equal to the dry starch particle size due to swelling. Exemplary dry particle sizes of some useful starches are 0.1 to 0.5 microns (dry). Exemplary starches are potato, corn, wheat, rice, and tapioca to list some non-limiting examples.

II. Controllable Slow Release Profile:

The prior art for producing iodine complexed PVA foam employs an "Entrapped Air Foaming Process" (see definitions). Namely, U.S. Pat. Nos. 5,071,648 and 6,365,169 utilized exclusively this air foaming process. This air foaming process results in an uncomplexed PVA foam density of 0.024 to a maximum of g/cm$^3$ (dry), with 0.030 to 0.050 g/cm$^3$ far more typical. Due to this relatively lower density, the foam is more porous and releases complexed iodine at a faster rate in comparison to the claimed invention. Using the shaker bath release testing method, as defined herein, samples produced by the U.S. Pat. No. 5,071,648 methodology at maximum densities [0.072 g/cm$^3$ (dry)] averaged 270 ppm at 3 hours, 350 ppm at 6 hours, and 450 ppm at 12 hours. In order to lower the ppm released using the U.S. Pat. No. 5,071,648 process, a lower initial content of complexed iodine must be used, which consequently reduces the duration of iodine release from this methodology. Surprisingly, the iodine released from the complexed PVA samples from the claimed invention is fully controllable based on the processing parameters and residual starch content without the need to reduce the initial iodine complexation load. It was determined through animal testing that 175 ppm at 3 hours, 300 ppm at 6 hours, and 400 ppm at 12 hours was a near maximum profile specifically for the claimed invention to optimize release duration. Further, it was determined that 50 ppm at 3 hours, 100 ppm at 6 hours, and 180 ppm at 12 hours was a near minimum to provide adequate iodine release to tissues specifically the claimed process. While the maximum release profile for the claimed invention within 50 ppm to U.S. Pat. No. 5,071,648 for 6 and 12 hours, the initial "burst" of iodine from the prior art samples provides significantly higher acute iodine toxicity. The prior art has not foreseen the advantages of this density range and residual starch content for limiting toxicity, controlling the profile of release, and extending iodine release duration. The unexpected positive results from the above composition, process, and density for animate tissues are specific to the pore former foaming process of the claimed invention.

The embodiments are further described by the following aspects:

1. A PVA foam article complexed with iodine, wherein said foam article exhibits controlled in vitro release of iodine in distilled water at 37 degrees Celsius of not less than about 3% after 3 hours, and after application to the tissues of a patient is capable of maintaining the release of iodine for at least 24 hours to reduce the frequency of article changes and patient discomfort and pain attributed to such changes.

2. The article according to item 1, wherein the fraction of iodine that is released in vitro is not less than about 6% after 6 hours.

3. The article according to item 1, wherein the fraction of iodine that is released in vitro is not less than about 10% after 12 hours.

4. The article according to item 1, wherein the fraction of iodine that is released in vitro is less than about 17% after 3 hours.

5. The article according to item 1, wherein the fraction of iodine that is released in vitro is less than about 31% after 6 hours.

6. The article according to item 1, wherein the fraction of iodine that is released in vitro is less than about 44% after 12 hours.

7. The article according to item 1, wherein the fraction of iodine that is released in vitro is from about 10 to about 20% after 6 hours.

8. The article according to item 1, wherein the fraction of iodine that is released in vitro is from about 20 to about 30% after 12 hours.

9. The article according to item 1, wherein the fraction of iodine that is released in vitro is more than about 25% after 16 hours.

10. The article according to item 1, wherein the fraction of iodine that is released in vitro is not more than about 10% after 1 hour, from about 3 to about 17% after 3 hours, and not less than about 10% after 12 hours.

11. The formulation according to item 1, wherein the in vitro release is measured by an iodine release test which utilizes:
a) a shaker bath,
b) a lateral agitation distance of 0.5 inches,
c) a release media of deaerated distilled water at 37 degrees Celsius,
d) a media volume of 18 ml per vessel,
e) media/sample vessels of a 1 inch diameter glass vials of approximately 20 ml volume,
f) an agitation rate equivalent to forty 0.5 inch lateral shifts per minute, and
g) a sample as supplied to a patient, sized to a surface area of 4.5 centimeters squared.

The embodiments are further described by the following aspects:

1. A PVA foam article complexed with iodine, wherein said foam article exhibits controlled in vitro release of iodine in distilled water at 37 degrees Celsius of not less than about 50 ppm after 3 hours, and after application to the tissues of a patient is capable of maintaining the release of iodine for at least 24 hours to reduce the frequency of article changes and patient discomfort and pain attributed to such changes.

2. The article according to item 1, wherein the amount of iodine that is released in vitro is not less than about 100 ppm after 6 hours.

3. The article according to item 1, wherein the amount of iodine that is released in vitro is not less than about 180 ppm after 12 hours.

4. The article according to item 1, wherein the amount of iodine that is released in vitro is less than about 175 ppm after 3 hours.

5. The article according to item 1, wherein the amount of iodine that is released in vitro is less than about 300 ppm after 6 hours.

6. The article according to item 1, wherein the amount of iodine that is released in vitro is less than about 400 ppm after 12 hours.

7. The article according to item 1, wherein the amount of iodine that is released in vitro is from about 100 to about 250 ppm after 6 hours.

8. The article according to item 1, wherein the amount of iodine that is released in vitro is from about 200 to about 400 ppm after 12 hours.

9. The article according to item 1, wherein the amount of iodine that is released in vitro is more than about 200 ppm after 16 hours.

10. The article according to item 1, wherein the amount of iodine that is released in vitro is not more than about 50 ppm after 1 hour, from about 50 to about 150 ppm after 3 hours, and not less than about 200 ppm after 12 hours.

11. The formulation according to item 1, wherein the in vitro release is measured by an iodine release test which utilizes:
a) a shaker bath,
b) a lateral agitation distance of 0.5 inches,
c) a release media of deaerated distilled water at 37 degrees Celsius,
d) a media volume of 18 ml per vessel,
e) media/sample vessels of a 1 inch diameter glass vials of approximately 20 ml volume,
f) an agitation rate equivalent to forty 0.5 inch lateral shifts per minute, and
g) a sample as supplied to a patient, sized to a surface area of 4.5 centimeters squared.

III. Extended Release Duration:

Surprisingly, the iodine released from the complexed PVA samples from the claimed invention is fully controllable based on the processing parameters and residual starch content without the need to reduce the initial iodine complexation load. It was determined through animal testing that an in vitro release of 175 ppm at 3 hours, 300 ppm at 6 hours, and 400 ppm at 12 hours was a near maximum profile specifically for the claimed invention to optimize release duration. Further, it was determined that an in vitro release of 50 ppm at 3 hours, 100 ppm at 6 hours, and 180 ppm at 12 hours was a near minimum to provide adequate iodine release to tissues specifically the claimed process. This ability to extend the release duration through the combination of PVA with residual starch complexation is specific to the claimed invention. The prior art has not foreseen the advantages of this density range and residual starch content for extending the duration of release from complexed iodine PVA foams, thereby providing for less dressing or device changes and less patient pain from such changes.

IV. No Potential for Excess Iodine:

The prior art for producing iodine complexed PVA foam (U.S. Pat. Nos. 5,071,648 and 6,365,169) both provide significant risk of excess iodine retention after the complexation step is executed as indicated and cautioned within the specifications of these patents. This is in part due to due to their reliance upon saturation complexation as well as their lack of a residual starch component. Surprisingly, the complexation process of the current invention does not result in excess iodine and thus the requirement of exhaustive wash out cycles or the risk of toxicity from this free, uncomplexed iodine. Presumably the residual starch remaining in the PVA foam after the pore former foaming process scavenges the residual excess iodine eliminating the excessive free iodine that drives acute toxicity. The prior art has not foreseen the advantages of this pore former foaming process with respect to the lack of excess iodine potential.

V. Improvements Via Lipid Semi-Solid Component:

In an effort to further decrease patient pain, lipid based semi-solids were combined with the iodine complexed PVA foam of the present invention. An exemplary example is LipoGel® Advance Wound Dressing, a commercial gel composition composed primarily of lipids, the majority of which is a liquid crystal forming lipid. It was envisioned that lipid based semi-solids would minimize patient pain by providing a thin gel interface with diseased tissue. However, it was also presumed that such lipid-based gels would inhibit the release of iodine by their hydrophobic nature. Further, LipoGel® is known in practice to be physically incompatible with other complexed iodine dressings currently supplied commercial (gel becomes partially hardened a agglomerated) preventing their use in combination. Quite surprisingly, the combination of LipoGel® and the iodine complexed foam as claimed in this invention demonstrated no physical incompatibility. More surprisingly, upon experimentation, this combination did not appreciably inhibit iodine release from the claimed invention. Even more surprisingly, the release of iodine from the combination provided near zero order release profiles of iodine, which make the release by hour a very advantageous constant rate. The in vitro release for the complexed PVA foam of the claimed invention in combination with the lipid-based semi-solid was 30 ppm at 3 hours, 60 ppm at 6 hours, and 110 ppm at 12 hours. This release profile demonstrated the added unexpected advantage of extending the duration of release even further, and at a near constant rate, while still providing clinically relevant iodine concentration in a combination that is easy to apply and readily available without adding complexity to the manufacturing process. The prior art has not foreseen the advantages of this pore former foaming process in combination with lipid based semisolids such as LipoGel® with respect to the compatibility of iodine release with this hydrophobic gel system as well as the advantages of pain reduction and near zero order release character. The prior art has not foreseen the resolution of physical incompatibilities with the combination of the claimed invention and lipid based semisolids.

EXAMPLES

Example 1

In a kettle fitted with a rotary mixer and slow rotation sweeper blades, hydrolyzed PVA resin was slurried in water, heated to a final temperature of about 80 to 90 C to solubilize the resin. A separate slurry of starch (corn starch in this example) and water were heated to a final temperature of about 80 to 90 C to partially solubilize the pore former. The two liquids were combined under constant agitation without entraining air and allowed to deaerate and cool to about 45 C. First an acid catalyst (i.e. sulfuric acid at 50% concentration) was added and mixed for approximately 10 minutes. Subsequently an aldehyde polymerizing agent (formaldehyde at 37%) was added under slow agitation to distribute polymerizing agent efficiently for uniform polymerization of the PVA resin. Agitation was carefully monitored so that at no time was significant air allowed to be entrained in the mix. The mix was discharged into a mold and cured in a warm oven (about 50 degrees Celsius) overnight to a final polymerization. The mold was then opened and the PVA foam was washed to remove residual chemicals and most of the starch, while leaving a residual amount of starch for subsequent complexation. The density of the cured foam was recorded as about 0.101 g/cm$^3$ (determined in dry state).

The remaining damp sponge was frozen and skived into 2.5 mm thick sheets. The resulting PVA sheets were subsequently die cut into 4 inch by 4 inch units. The units were subsequently complexed with iodine under constant agitation at room temperature to produce a uniformly black 4×4 iodine complexed foam articles. The complexation step was controlled via metered complexation to prevent free excess iodine. At the conclusion of the metered step, the agitation continued for 30 minutes to eliminate any potential free excess iodine. Finally the units were packaged damp with a moisture content of about 70%.

Iodine Release Profile for Example 1 Material:

Through various testing, and as disclosed herein, the maximum release profile for this specific type of complexed PVA foam was determined to be about 175 ppm at 3 hours, 275 ppm at 6 hours and 380 ppm at 12 hours. Such a profile maximizes iodine impact on microbes, however it minimizes the duration of release in this specific claimed invention. Through various testing, and as disclosed herein, the minimum release profile for this specific type of complexed PVA foam was determined to be about 50 ppm at 3 hours, 100 ppm at 6 hours and 180 ppm at 12 hours. Such a profile provides the minimum iodine impact on microbes considered efficacious, however it maximizes the duration of release in this specific claimed invention. It should be noted that one can alter the processing to produce complexed foams that produce profiles near the upper limit referenced above if high iodine potency is desired, or alternatively one can alter the processing parameters to produce the minimum profile if the longest duration is desired. PVA article designs for treatment strategies are logically targeted higher (maximum profile), while preventative strategies are targeted lower (minimum profile). In this specific example, the intention was to target the middle of the profile, which neither maximizes potency/efficacy nor minimizes duration (i.e. good efficacy and good duration). Therefore, this example was prepared a priori, based on known inputs of process, including residual starch level, iodine load, and the complexation duration, to deliver a release profile within those profile limits.

The results of the release testing for Example 1, using the shaker bath as specified herein:

|  | Hour | | | | |
| --- | --- | --- | --- | --- | --- |
|  | 1 | 3 | 6 | 12 | 16 |
| ppm released | 35.0 | 101.9 | 169.1 | 265.6 | 295 |
| % released | 3.5 | 10.2 | 16.9 | 26.6 | 29.5 |

ISO Biocompatibility Testing, Including Cytotoxicity Demonstrated:

1. The uncomplexed PVA foam produced by Example 1 containing residual starch by design and intent, unexpectedly passed all cytotoxicity and irritation testing with the lowest scores possible (effectively no incompatibility detected, or equivalent to known non-toxic controls).

2. Cytotoxicity testing for the same PVA foam after complexation with iodine demonstrated identical cytotoxicity scores to currently marketed slow release iodine products (not foam products) and markedly lower than iodine tinctures for acute exposure. This testing demonstrates the value and achievement of some pivotal objectives of the invention, namely release profiles of iodine that can limit iodine toxicity to commercializable levels, while not imparting additional toxicities from the residual carbohydrates employed to generate those extended profiles.

Negative Pressure Wound Therapy:

The resulting density of the claimed invention provides for thin thicknesses that still retain adequate strength. Sheets as thin as 1 mm have were used successfully with negative pressure wound therapy, combining the benefits of iodine releasing foams with negative pressure for the first time in practice. The uncomplexed PVA foam produced by Example at about 2.5 mm thickness also proved exemplary for combination with negative pressure wound therapy.

Example 2

Release Profiles with Maximum and Minimum Boundaries Targeted

As described in Example 1, the processing may be altered to produce complexed foams of the claimed invention that produce profiles that span the boundaries claimed. The critical inputs variables that alter profiles include the residual starch level, the type of starch, the polymerization aldehyde level, the temperature of the carbohydrate slurry, iodine load, and the duration and mixing efficiency of the iodine complexation step.

The results of the release testing for two more lots produced under altered processing variables are listed below. These lots were executed to demonstrate the excellent control and predictability of the resulting profiles. The results are in quite strong alignment with the targeted maximum and minimum profiles. All release testing employed the shaker bath methodology as specified herein:

| Lot MX032615 | | | | | |
|---|---|---|---|---|---|
| | Hour | | | | |
| | 1 | 3 | 6 | 12 | 16 |
| ppm Released | 46.8 | 174.8 | 277.5 | 376.1 | 412.0 |

| Lot MN032615 | | | | | |
|---|---|---|---|---|---|
| | Hour | | | | |
| | 1 | 3 | 6 | 12 | 16 |
| ppm Released | 16.2 | 54.7 | 103.6 | 211.4 | 231.3 |

Products Contemplated

Products for disinfection of surfaces. Products for disinfection of liquids. Products for microbial bioburden management on bodily tissues, including negative pressure wound therapy.

Although the present invention has been described in relation to a particular embodiment thereof, many other variations and other uses will become apparent to those skilled in the art. It is preferred, therefore, that the present invention be limited not by the specific disclosure herein, but only by the appended claims.

What claimed is:

1. A method for treating a wound of a patient in need thereof, said method comprising:
    (a) providing a polyvinyl alcohol (PVA) foam article comprising an iodophor, wherein the PVA foam article has a density of at least 0.078 g/cm³, wherein the PVA foam article comprises PVA foam, starch, and iodine; wherein the iodine is complexed at least in part to the PVA foam and the starch to form said iodophor; and
    (b) applying the PVA foam article to a tissue of the patient for at least 24 hours, wherein the tissue has a wound.

2. The method according to claim 1, wherein the PVA foam article has a thickness of from 2 millimeters to 6 millimeters.

3. The method according to claim 1, wherein the PVA foam article is packaged before application with a moisture content of at least 40% (w/w).

4. The method according to claim 1, wherein the PVA foam article further comprises a lipid-based semisolid, which is composed of liquid crystal forming lipid, added to the PVA foam article prior to packaging or at the time of application to the patient such that iodine has a release profile nearer to zero order than to first order.

5. The method according to claim 1 further comprising using negative pressure wound therapy in combination with the PVA foam article.

6. A method for treating a wound of a patient in need thereof, said method comprising:
    (a) providing a polyvinyl alcohol (PVA) foam dressing comprising an iodophor, wherein the PVA foam dressing has a density of at least 0.078 g/cm³, wherein the PVA foam dressing is produced by a method comprising: mixing PVA and a starch pore former in a slurry, adding an aldehyde to the slurry to produce a foam, and washing the foam to produce a PVA foam containing residual starch, and complexing iodine at least in part to the PVA foam and the residual starch to form said iodophor; and
    (b) applying the PVA foam dressing to a tissue of the patient, wherein the tissue has a wound.

7. The method according to claim 6, wherein the starch is less than 30% of the PVA foam dressing.

8. The method according to claim 7, wherein the starch has an average particle size of from 0.1 microns to 0.6 microns prior to hydration.

9. The method according to claim 6, wherein the PVA foam dressing has a thickness of from 2 millimeters to 6 millimeters.

10. The method according to claim 6, wherein the PVA foam dressing is packaged before application with a moisture content of at least 40% (w/w).

11. The method according to claim 6 further comprising using negative pressure wound therapy in combination with the PVA foam dressing.

12. The method according to claim 6, wherein the PVA foam dressing further comprises a lipid-based semisolid, which is composed of liquid crystal forming lipid, added to the PVA foam article prior to packaging or at the time of application to the patient such that iodine is released at a nearly constant rate.

13. A method for delivering iodine to a patient in need thereof, wherein the method releases iodine for at least 24 hours as an effective antimicrobial agent; said method comprising:
    (a) providing a biocompatible polyvinyl alcohol (PVA) foam dressing comprising (i) PVA foam, (ii) residual starch within the PVA foam, and (iii) iodine; wherein the iodine is complexed at least in part to the PVA and the residue starch to form an iodophor; and
    (b) applying the PVA foam dressing to a tissue of the patient, wherein the tissue has a wound.

14. The method according to claim 13, wherein the starch is less than 30% of the PVA foam dressing.

15. The method according to claim 14, wherein the starch has an average particle size of from 0.1 microns to 0.6 microns.

16. The method according to claim 13, wherein the PVA foam dressing has a thickness of from 2 millimeters to 6 millimeters.

17. The method according to claim 13, wherein the PVA foam dressing is packaged before application with a moisture content of at least 40% (w/w).

18. The method according to claim 13 further comprising using negative pressure wound therapy in combination with the PVA foam dressing.

19. The method according to claim 13, wherein the PVA foam dressing is produced by a method comprising:
(a) mixing PVA resin, starch, and water in a slurry,
(b) adding an aldehyde to the slurry,
(c) curing the product of the PVA resin, starch pore former, and aldehyde,
(d) washing the cured product of (c) to remove a portion of the starch, forming pores therein to provide a PVA foam having a density of at least 0.074 g/cm$^3$ and residual starch, and
(e) complexing iodine with the PVA and the residue starch to provide the PVA foam dressing.

20. A method for treating a wound of a patient in need thereof, said method comprising:
(a) providing an iodophor comprising PVA foam, a starch, and iodine; said PVA foam and starch in solid form, both PVA and starch complexed with iodine; and
(b) applying the iodophor to a tissue of the patient, wherein the tissue has a wound.

21. The method according to claim 20, wherein the duration of iodine release upon applying the iodophor is at least 24 hours.

22. The method according to claim 20, wherein the amount of starch is controlled in part by providing an initial PVA resin and starch mix that is about 30% w/w starch prior to addition of an aldehyde.

23. The method according to claim 20, wherein the duration of release is controlled in part by providing an initial iodine load between about 2% and 8% w/w.

24. The method according to claim 20, wherein the release profile of the iodophor is controlled in part by
(a) controlling an amount of starch within the foam article by an initial PVA resin and starch mix that is about 30% w/w starch prior to addition of an aldehyde thereby entrapping the starch in part,
(b) further controlling the degree of entrapment by beginning complexation of the PVA and starch with iodine after the aldehyde has been added to the PVA resin—starch mix, and
(c) providing an initial iodine load of about 2% to 8% w/w.

25. The method according to claim 24, wherein the aldehyde is formaldehyde.

26. The method according to claim 21, wherein the release profile of the iodophor is controlled in part by
(a) controlling an amount of starch content within the foam article provided by an initial PVA resin and starch mix that is about 30% w/w starch prior to addition of an aldehyde thereby entrapping the starch in part,
(b) further controlling the degree of entrapment by beginning the complexation of the PVA and starch with iodine after the aldehyde has been added to the PVA resin—starch mix, and
(c) providing an initial iodine load between about 2% and 8% w/w at the start of treatment.

27. The method according to claim 26, wherein the aldehyde is formaldehyde.

28. The method of claim 1, wherein the starch is potato starch or corn starch.

* * * * *